United States Patent [19]

Randell et al.

[11] 4,038,280

[45] July 26, 1977

[54] HYDROXYARYL-TETRAMETHYL-PIPERIDINES

[75] Inventors: Donald Richard Randell, Stockport; Malcolm John Smith, Marple, both of England

[73] Assignee: Ciba-Geigy Corporation, Ardsley, N.Y.

[21] Appl. No.: 310,060

[22] Filed: Nov. 28, 1972

[30] Foreign Application Priority Data

Nov. 30, 1971 United Kingdom ............... 55419/71
July 14, 1972 United Kingdom ............... 32947/72

[51] Int. Cl.$^2$ .......................................... C07D 211/22
[52] U.S. Cl. ......................... 260/293.84; 260/45.9 R; 260/293.62; 260/293.63; 260/293.64; 260/293.66; 260/293.67; 260/293.68; 260/293.74; 260/293.82; 260/293.83; 252/402; 252/403
[58] Field of Search .................... 260/293.62, 293.63, 260/293.64, 293.66, 293.67, 293.68, 293.74, 293.82, 293.83, 293.84

[56] References Cited

U.S. PATENT DOCUMENTS

| | | | |
|---|---|---|---|
| 2,498,430 | 2/1950 | Lee | 260/294 |
| 3,431,232 | 3/1969 | Murayama et al. | 260/45.8 |
| 3,436,369 | 4/1969 | Kitaoka et al. | 260/45.8 |
| 3,448,074 | 6/1969 | Kitaoka et al. | 260/45.8 |
| 3,503,982 | 3/1970 | Murayama et al. | 260/293 |
| 3,513,170 | 5/1970 | Murayama et al. | 260/294.7 |
| 3,532,703 | 10/1970 | Murayama et al. | 260/294 |
| 3,534,048 | 10/1970 | Murayama et al. | 260/293 |
| 3,542,729 | 11/1970 | Murayama et al. | 260/45.8 |
| 3,733,326 | 5/1973 | Murayama et al. | 260/290 V |
| 3,734,883 | 5/1973 | Holt | 260/45.8 N |
| 3,954,779 | 5/1976 | Smith et al. | 260/293.65 |

*Primary Examiner*—Cecilia M. S. Jaisle
*Attorney, Agent, or Firm*—Nestor W. Shust; C. W. Vanecek

[57] ABSTRACT

New 4-(4'-hydroxyaryl)-2,2,6,6-tetramethyl-piperidines are used as stabilisers for organic materials, especially for polymers.

8 Claims, No Drawings

HYDROXYARYL-TETRAMETHYL-PIPERIDINES

The present invention relates to new piperidine derivatives and in particular to new 4-(4'-hydroxyaryl)-2,2,6,6-tetramethyl piperidines which are useful stabilisers for polymers.

According to the present invention, there are provided compounds having the general formula I:

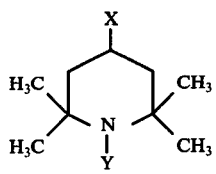

and salts thereof wherein the substituent X has one of the formulae II and III:

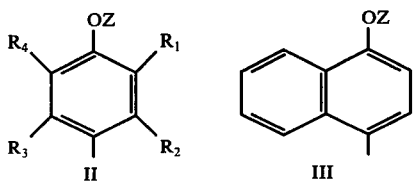

preferably the formula II, $R_1$, $R_2$, $R_3$ and $R_4$ in formula II being the same or different and each being hydrogen, a straight- or branched chain alkyl residue having from 1 to 9, preferably 1 to 4 carbon atoms, a cycloalkyl residue having from 5 to 14, preferably 6 to 8 carbon atoms, an aralkyl residue having from 7 to 14, preferably 7 to 9 carbon atoms, or an aryl or alkaryl residue each having from 6 to 14, preferably 6 to 10 carbon atoms, Y is hydrogen, O, a straight- or branched alkyl residue having from 1 to 12 carbon atoms, an alkenyl or alkynyl residue having from 3 to 12 carbon atoms or an aralkyl residue having from 7 to 12 carbon atoms, Z is hydrogen, an alkyl or substituted alkyl residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 12 carbon atoms, an aromatic residue having from 6 to 12 carbon atoms or a heterocyclic residue, or the group —$COZ_1$ wherein $Z_1$ has the same significance as Z, or $Z_1$ is a group

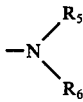

wherein $R_5$ is hydrogen or an alkyl residue having from 1 to 4 carbon atoms and $R_6$ is hydrogen, an aliphatic residue having from 1 to 20 carbon atoms, a cycloaliphatic residue having from 5 to 12 carbon atoms or an aromatic residue having from 6 to 12 carbon atoms.

Examples of substituents $R_1$, $R_2$, $R_3$ and $R_4$ are methyl, ethyl, n-propyl, isopropyl, sec. butyl, t-butyl, sec. amyl, t-amyl (1,1-dimethyl butyl), capryl (2-octyl), isononyl, (ex mixed isometric nonenes), cyclohexyl, 1-methyl cyclohexyl, cyclooctyl, adamantyl, cyclododecyl, benzyl, α-methylbenzyl, α,α-dimethylbenzyl, phenyl and naphthyl residues. Preferred substituents $R_1$, $R_2$, $R_3$ and $R_4$ are, however, hydrogen, methyl, ethyl, n-propyl, isopropyl, sec. butyl, t-butyl, 1,1-dimethylpropyl, 1,1-dimethylbutyl, 2-octyl, cyclohexyl, 1-methyl cyclohexyl, benzyl, α,α-dimethylbenzyl and phenyl residues.

Examples of particular combinations of substituents $R_1$, $R_2$, $R_3$ and $R_4$ are set out in the following Table.

Table

| $R_1$ | $R_2$ | $R_3$ | $R_4$ |
|---|---|---|---|
| H | H | H | H |
| CH₃ | H | H | H |
| H | CH₃ | H | H |
| CH₃ | H | CH₃ | H |
| CH₃ | H | H | CH₃ |
| CH₃ | CH₃ | CH₃ | CH₃ |
| C₂H₅ | H | H | H |
| H | C₂H₅ | H | H |
| H | C₂H₅ | CH₃ | H |
| C₂H₅ | H | H | C₂H₅ |
| n-C₃H₇ | H | H | H |
| n-C₃H₇ | H | H | n-C₃H₇ |
| iso-C₃H₇ | H | H | H |
| H | iso-C₃H₇ | H | H |
| iso-C₃H₇ | H | H | iso-C₃H₇ |
| sec-C₄H₉ | H | H | H |
| sec-C₄H₉ | H | H | sec-C₄H₉ |
| t-C₄H₉ | H | H | H |
| H | t-C₄H₉ | H | H |
| t-C₄H₉ | H | CH₃ | H |
| t-C₄H₉ | H | H | CH₃ |
| t-C₄H₉ | H | H | t-C₄H₉ |
| sec-amyl | H | H | H |
| sec-amyl | H | H | sec-amyl |
| 1,1-dimethylpropyl | H | H | H |
| 1,1-dimethylpropyl | H | H | 1,1-dimethylpropyl |
| 1,1-dimethylbutyl | H | H | H |
| 1,1-dimethylbutyl | H | H | 1,1-dimethylbutyl |
| 2-octyl | H | H | H |
| cyclohexyl | H | H | H |
| 1-methylcyclohexyl | H | H | H |
| benzyl | H | H | H |
| α,α-dimethylbenzyl | H | H | H |
| phenyl | H | H | H |

Thus, although, in particular instances, each of the substituents $R_1$, $R_2$, $R_3$ and $R_4$ may be other than hydrogen, for instance, they may each be methyl, it is preferred in general, that at least two of these substituents are hydrogen. In particular, it is preferred that $R_2$ and/or $R_3$ are non-bulky substituents for instance a hydrogen atom, methyl or ethyl groups. However, if when one of the substituents $R_2$ and $R_3$ is a bulky group such as t-butyl group, then the other substituent is preferably hydrogen. Furthermore, it is to be understood that it is unlikely that bulky groups such as t-butyl groups will be situated on adjacent carbon atoms of the phenyl residue.

Apart from O, and hydrogen Y may also be a methyl, ethyl, n-propyl, isopropyl, n-butyl, sec-butyl, n-hexyl, n-octyl, n-dodecyl, allyl, α-methallyl, 10-undecenyl, benzyl, α-methylbenzyl, p-methylbenzyl or an α-naphthyl-benzyl residue. However, particularly preferred substituents Y are O and straight- or branched alkyl groups having from 1 to 4 carbon atoms, the most preferred substituents Y being O, hydrogen and methyl residues.

Preferably, Z is hydrogen.

Examples of alkyl or substituted alkyl residues Z are methyl, ethyl, n-propyl, n-butyl, sec-butyl, t-butyl, n-hexyl, n-octyl, 2-ethylhexyl, n-nonyl, n-decyl, n-undecyl, n-dodecyl, n-tridecyl, n-tetradecyl, n-hexadecyl, n-octadecyl eicosyl β-hydroxyethyl and β-cyanoethyl residues. Preferred alkyl or substituted alkyl residues Z are those having from 1 to 12 carbon atoms.

When Z is an alkenyl residue having from 3 to 20 carbon atoms, examples of such residues are allyl, methallyl, 3-hexenyl, 4-octenyl, 6-decenyl, 10-undecenyl and 8-octadecenyl residues, preferred alkenyl residues Z being allyl and methallyl residues.

Examples of alkynyl residues Z are propargyl, but-1- and -2- ynyl, pent-1-ynyl, hex-1-ynyl, oct-1-ynyl, dec-1-ynyl, dodec-1-ynyl, tetradec-1-ynyl and octadec-1-ynyl, preferred alkynyl residues Z being propargyl and methyl propargyl residues.

When Z is a cycloalkyl residue, it may be a cyclooctyl or cyclodecyl residue but is preferably a cyclopentyl or cyclohexyl residue.

Araliphatic residues Z may be, for instance, benzyl, $\alpha,\alpha$-dimethylbenzyl or $\alpha$-methylbenzyl residues.

Aromatic residues Z include phenyl, tolyl, naphthyl and p-t-butylphenyl residues.

Heterocyclic residues Z includes furan and thiophene residues.

When $Z_1$ is a group having the formula -$NR_5R_6$, examples of such residues are carbamoyl, N-methylcarbamoyl, N-ethyl-carbamoyl, N-n-propylcarbamoyl, N-isopropylcarbamoyl, N-n-butylcarbamoyl, N-n-pentylcarbamoyl, N-n-octylcarbamoyl, N-n-decylcarbamoyl, N-n-dodecylcarbamoyl, N-n-octadecyl, N-n-eicosylcarbamoyl, N-allylcarbamoyl, N-methallylcarbamoyl, N-undecenylcarbamoyl, N-cyclopentylcarbamoyl, N-cyclohexylcarbamoyl, N-methyl-cyclohexylcarbamoyl, N-cyclododecylcarbamoyl, N-(1- and 2-perhydronaphthyl)carbamoyl, N-adamantylcarbamoyl, N-cyclopentylmethylcarbamoyl, N-benzylcarbamoyl, N-($\beta$-phenethyl)carbamoyl, N-(1- and 2-naphthylmethyl) carbamoyl, N-phenylcarbamoyl, N-(o-, m- and p-tolyl) carbamoyl, N-(2,4- and 2,6-xylyl)carbamoyl, N-($\alpha$- and $\beta$-naphthyl)carbamoyl, N,N-dimethylcarbamoyl, N-methyl, N-ethylcarbamoyl, N,N-diethylcarbamoyl, N,N-diisopropylcarbamoyl, N,N-di-n-propylcarbamoyl, N,N-di-n-butyl, carbamoyl and N,N-diisobutyl-carbamoyl residues.

Examples of salts are those formed from the amine function of the compounds of formula I with inorganic or organic acids, for instance hydrogen chloride, sulphuric acid, phosphoric acid, carbonic acid, acetic acid, maleic acid, malic acid, oxalic acid and tartaric acid, as well as salts formed from the phenolic function with metals, for instance alkali metals such as sodium and potassium, alkaline earth metals such as calcium, magnesium or barium, or cadmium or lead or nickel.

Examples of compounds of formula I are:

Where Z = hydrogen, Y = hydrogen
4-(4'-hydroxyphenyl)-2,2,6,6-tetramethylpiperidine
4-(3'5=-dimethyl-4'-hydroxyphenyl)2,2,6,6-tetramethylpiperidine
4-(3'-methyl-4'-hydroxyphenyl)-2,2,6,6-tetramethylpiperidine
4-(4'-hydroxynaphthyl)-2,2,6,6-tetramethylpiperidine
4-(3'-cyclohexyl-4'-hydroxyphenyl)-2,2,6,6-tetramethylpiperidine
4-(340 -t-butyl-4-hydroxyphenyl)-2,2,6,6-tetramethyl-piperdine 4-(3'5'-Di-isopropyl-4'-hydroxyphenyl)-2,2,6,6-tetramethylpiperidine
4-(3'-t-butyl-4'-hydroxy-5'-methylphenyl)-2,2,6,6-tetramethylpiperidine
4-(3'5'-Di-t-butyl-4'-hydroxyphenyl)-2,2,6,6-tetramethylpiperidine
4(3'-Benzyl-4'-hydroxyphenyl)-2,2,6,6-tetramethyl piperidine Z = hydrogen, Y = O
4-(3'5'-Dimethyl-4'-hydroxyphenyl)-2,2,6,6-tetramethylpiperidine-1-oxyl.
4-(4'-hydroxyphenyl)-2,2,6,6-tetramethyl-piperidine-1-oxyl.

Z= hydrogen, Y = hydrocarbyl
4-(4'-Hydroxyphenyl)-1,2,2,6,6-pentamethyl piperidine
4-(3'5'-Dimethyl-4'-hydroxyphenyl)-1,2,2,6,6-pentamethylpiperidine
1-allyl-4(3'5'-dimethyl-4'-hydroxyphenyl)-2,2,6,6-tetramethyl piperidine
1-Benzyl-4(4'-hydroxyphenyl)-2,2,6,6-tetramethyl piperidine
1-n-Dodecyl-4(3'-phenyl-4'-hydroxyphenyl)-2,2,6,6-tetramethylpiperidine
1-n-Hexyl-4(3'-cyclohexyl-4'-hydroxyphenyl)-2,2,6,6-tetramethylpiperidine $$Z = \underset{\underset{O}{\|}}{C}-Z_1 \ , \ Y = \text{hydrogen}$$

4(3'-cyclohexyl-4'-hexanoyloxyphenyl)-2,2,6,6-tetramethylpiperidine
4(3'5'-Dimethyl-4'-dodecanoyloxyphenyl)-2,2,6,6-tetramethylpiperidine
4(3'-t-Butyl-4'-stearoyloxyphenoyl)-2,2,6,6-tetramethylpiperidine
4(4'-n-Butyryloxy-3'-methylphenyl)-2,2,,6,6-tetramethylpiperidine
4(4'-Benzoyloxyphenyl)-2,2,6,6-tetramethylpiperidine
4-(3',5'-Dimethyl-4'-octanoyloxyphenyl)-2,2,6,6-tetramethylpiperidine
4-(4'-Acetyloxyphenyl)-2,2,6,6L -tetramethylpiperidine
4(4'-N-Methylcarbamoyloxyphenyl)-2,2,6,6-tetramethyl piperidine
4(4'-N-Butylcarbamoyloxy-3'L -methylphenyl) 2,2,6,6-tetramethylpiperidine
4(4'-N-hexylcrbamoyloxy-3'-methylphenyl) 2,2,6,6-tetramethyl piperidine
4(3',5'-dimethyl-4'-N-dodecylcarbamoyloxyphenyl)-2,2,6,6-tetramethylpiperidine
4(3'-t-Butyl-4'-oxtadecylcarbamoyloxyphenyl) 2,2,6,6-tetramethylpiperidine $$\text{Where } Z = \underset{\underset{O}{\|}}{C}-Z_1 \ , \ Y = O$$

4(4'-Acetyloxyphenyl)-2,2,6,6-tetramethylpiperidine-1-oxyl
4(3'-Cyclohexyl-4'-hexanoyloxyphenyl)-2,2,6,6-tetramethylpiperidine-1-oxyl
4(4'-N-Methylcarbamoyloxyphenyl)-2,2,6,6-tetramethylpiperidine-1-oxyl $$\text{Where } Z = \underset{\underset{O}{\|}}{C}-Z_1 \ , \ Y = \text{hydrocarbyl}$$

4(4'-Acetyloxyphenyl)-1,2,2,6.6-pentamethylpiperidine

4(4'-N-Methylcarbamoyloxyphenyl)-1,2,2,6,6-pentmethylpiperidine

Z = hydrocarbyl, Y = H

4(4'-methoxy phenyl)-2,2,6,6-tetramethylpiperidine
4(4'-n-Butyloxyphenyl)-2,2,6,6-tetramethylpiperidine
4-(4'-n-Dodecyloxyphenyl)-2,2,6,6-tetramethylpiperidine
4;L -(4'-Benzyloxyphenyl)-2,2,6,6-tetramethylpiperidine Where Z = hydrocarbyl, Y = 0°

4(4'-Methoxyphenyl)-2,2,6,6-tetramethylpiperidine-1-oxyl
4-(4'-n-Dodecyloxyphenyl)-2,2,6,6-tetramethylpiperidine-1-oxyl Where Z = hydrocarbyl, Y = hydrocarbyl 4(4'-Methoxyphenyl)-1,2,2,6,6-pentamethylpiperidine
4(4'-n-Dodecyloxyphenyl)-1,2,2,6,6-pentamethylpiperidine
4(4'-n-Butyloxyphenyl)-1-butyl-2,2,6,6-tetramethylpiperidine According to the present invention there is also provided a first process in which a compound of formula I is produced comprising hydrogenating a compound of formula IV

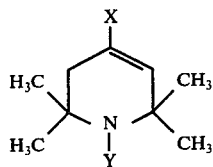

IV wherein X and Y have their previous significance, except that Y canot be 0° or an alkenyl residue.

The hydrogenation is conveniently effected in a solvent inert under the reaction conditions, for instance an aliphatic alcohol having from 1 to 4 carbon atoms, and in the presence of a hydrogenation catalyst for instance palladium, platinum, ruthenium, rhodium, or Raney nickel. The catalyst may be used in pure form or supported upon an inert carrier such as alumina, calcium carbonate or carbon.

Alternatively, the hydrogenation may be carried out using as starting material a salt of the compound of formula IV. The salt may be a salt of the amine function with an inorganic acid such as hydrogen chloride or an organic acid such as acetic acid; or a salt of the phenolic function with a metal, for instance an alkali metal such as sodium or potassium. When a salt of a compound of formula IV is used, the hydrogenation is preferably conducted in aqueous solution and the product of formula I is isolated by neutralisation of the aqueous solution with a base or acid as appropriate. Subsequently, if desired, the product may be further purified by conventional techniques such as cyrstallisation from a solvent.

Each of the hydrogenation procedures may be carried out under a wide variety of conditions for instance at ambient or elevated temperatures and pressures.

Compounds of formula I in which Y is 0° may be conveniently produced by reacting compounds of formula I in which Y is H with an oxidising agent such as hydrogen peroxide or a per-acid such as per-formic acid. Preferably the oxidation is conducted in aqueous or alcoholic solution and in the presence of an oxidation catalyst such as tungstic acid or sodium tungstate.

In a less preferred embodiment, an N-substituted compound of formula I for instance a compound of formula I wherein Y is methyl, may be oxidised to give the corresponding compound of formula I in which Y is 0°.

When the substituent Y in the compound of formula I is other than 0°, these derivatives may be produced by reacting the corresponding compound of formula I in which Y is hydrogen with an alkylating, alkenylating, alkynating or aralkylating agent such as alkyl, alkenyl, alkynyl or aralkyl halide respectively.

When Z is hydrogen in compound I then the group -OZ may require protection during the reaction to avoid undesirable simultaneous O-and N- substitution.

N-substitution derivatives may also be prepared by a Leuckart, Wallach or Eschweiler-Clarke reaction by reacting the compound of formula I wherein Y is H with formic acid and the appropriate aldehyde or ketone. In this way, for example, the N-Methyl derivative may be obtained using formic acid and formaldehyde.

Compounds of formula I in which Z is the group -COZ$_1$ where Z$_1$ is as hereinbefore defined may be conveniently prepared by reacting a compound of formula I in which Z is hydrogen with an esterification agent such as an acid, an acid chloride, an acid ester or an acid anhydride or an agent capable of forming a urethane grouping with the compound of formula I, such as an alkyl, alkenyl, aralkyl or aryl isocyanate.

The reaction is preferably conducted in a solvent inert under the reaction conditions such as benzene, toluene or xylene.

Compounds of formula I in which Y is as hereinbefore defined and Z is not hydrogen may be conveniently produced by reacting compounds of formula I in which Z is hydrogen with an alkali metal such as sodium or potassium followed by reaction with an alkylating, alkenylating, alkynylating or aralkylating agent such as an alkyl, alkenyl, alkynyl or aralkyl halide.

The reaction is preferably conducted in a solvent inert under the reaction conditions such as benzene, toluene or xylene.

The present invention still further provides a composition comprising an organic material and a minor proportion of a compound having the formula I as hereinbefore defined.

Compounds of formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methylbutene-1, hexene-1, 4-methylpentene-1, 4-methylhexene-1 and 4,4-dimethyl-pentene-1, and also co- and ter-polymers of olefines, particularly of ethylene or propylene.

Other organic materials susceptible to degradation by the effects of light and the properties of which are improved by the incorporation therein of a compound of Formula I include natural and synthetic polymeric materials, for instance natural and synthetic rubbers, the latter including, for example, homo-, co- and terpolymers of acrylonitrile, butadiene and styrene.

Specific synthetic polymers include polyvinyl chloride, polyvinylidene chloride and vinyl chloride copolymers, polyvinyl acetate as well as condensation polymers derived from ether, ester (derived from carboxylic sulphonic or carbonic acids), amide or urethane groupings. These polymers can, for instance, form the basis of surface coating media such as paints and lacquers having an oil or resin, for instance an alkyd or polyamide resin, base.

The amount of the compound of formula 1 which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound of formula I may be added to the polymer during the preparation of the latter, for instance at the latex stage of polymer production, to provide pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binoxy, tertiary and multi-component compositions containing the stabiliser of formula I together with one or more functional additives for polymers.

Examples of suitable antioxidants are those of the hindered phenol type such as those selected from the following groups:

1. Phenolic compounds having the general formula $$Q-(CH_2)_w - A_1$$

wherein
Q is

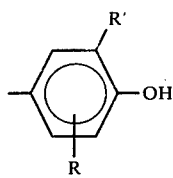

$A_1$ is $CR(COOR'')_2$

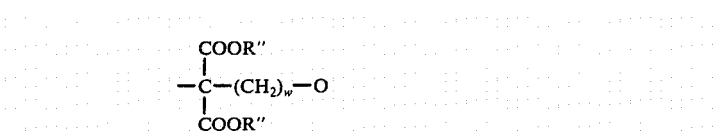

R — is hydrogen or lower alkyl
R' — is lower alkyl
R" — is alkyl group having from 6–24 carbon atoms
W — is an integer from 0 to 4.

Illustrative examples of the compounds shown above are di-n-octadecyl α-(3,5-di-t-butyl-4-hydroxy-benzyl)-malonate di-n-octadecyl α-(3-t-butyl-4-hydroxy-5-methyl-benzyl)malonate which is disclosed in the Netherlands Pat. No. 6,711,199, Feb. 19, 1968.

di-n-octadecyl-α,α'bis-(3-t-butyl-4-hydroxy-5-methylbenzyl)malonate which is disclosed in the Netherlands Pat. No. 6,803,498, Sept. 18, 1968.

2. Phenolic compounds having the general formula $$Q - R$$

Illustrative examples of the compounds shown above are
2,6-di-t-butyl-p-cresol
2-methyl-4,6-di-t-butylphenol and the like.
2,6-di-oxtadecyl-p-cresol.

3. Phenolic compounds having the formula $$Q-C_wH_{2w}-Q$$

Illustrative examples of the compounds shown are:
2,2'-methylene-bis-(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(2-t-methylcyclohexyl)]-4-methylphenol
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol) and the like.

4. Phenolic compounds having the formula $$R-O-Q$$

Illustrative examples of such compounds are
2,5-di-t-butylhydroquinone
2,6-di-t-butylhydroquinone
2,5-ti-t-butyl-4-hydroxyanisole.

5. Phenolic compounds having the formula $$Q-S-Q$$

Illustrative examples of such compounds are
4,4'-thiobis-(2-t-butyl-5-methylphenol)
4,4'-thiobis-(2-t-butyl-6-methylphenol)
2,2'-thiobis-(6-t-butyl-4-methylphenol)
4,4'-thiobis-(2-methyl-5-t-butylphenol).

6. Phenolic compounds having the formula $$Q-(CH_2)_w-S-(CH_2)_w-\overset{\overset{\displaystyle O}{\|}}{C}-OR''$$

Illustrative examples of such compounds are
octadecyl-(3,5-dimethyl-4-hydroxybenzylthio)-acetate dodecyl-(3,5-di-t-butyl-4-hydroxybenzylthio)-propionate.

7. Phenolic compounds having the formula

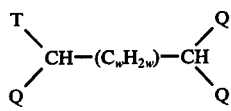

wherein T is hydrogen
R or Q as defined above.
Illustrative examples of such compounds are
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane.

8. Phenolic compounds having the formula

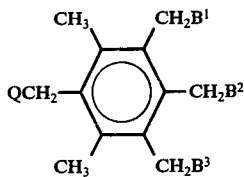

wherein $B^1$, $B^2$ and $B^3$ are hydrogen, methyl or Q provided that when $B^1$ and $B^3$ are Q then $B^2$ is hydrogen or methyl and when $B^2$ is Q then $B^1$ and $B^3$ are hydrogen or methyl.

Illustrative examples of such compounds are
1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene.

9. Phenolic compounds having the formula

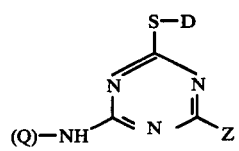

wherein Z is NHQ, -S-D or -O-Q
D is alkyl group having from 6 – 12 carbon atoms or $-(C_wH_{2w})-S-R''$.

Illustrative examples of such compounds are
2,4-bis-(n-octylthio)-6-(3,5-di-t-butyl-4-hydroxyaniline)-1,3,5-triazine
6-(4-hydroxy-3-methyl-5-t-butylanilino)-2,4-bis-(n-octylthio)-1,3,5-triazine
6-(4-hydroxy-3,5-dimethylanilino)-2,4-bis-(n-octylthio)-1,3,5-triazine
6-(4-hydroxy-3,5-di-t-butylanilino)-2,4-bis-(n-octylthio)-1,3,5-triazine.
6-(4-hydroxy-3,5-di-t-butylanilino)-4-(4-hydroxy-3,5-di-t-butylphenoxy)-2-(n-octylthio) 1,3,5-triazine
2,4-bis(4-hydroxy-3,5-di-t-butylanilino)-6-(n-octylthio)-1,3,5-triazine.

The above phenolic triazine stabilizers are more fully described in U.S. Pat. No. 3,255,191.

10. Phenolic compounds having the formula

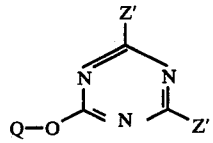

wherein Z' is —O—Q, —S—D or —S—$(C_wH_{2w})$—SD.
Illustrative examples of such compounds are
2,3-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine
6-(4-hydroxy-3,5-di-t-butylphenoxy)-2,4-bis-(n-octylthioethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.

The above phenolic triazine stabilizers are more fully described in U.S. Pat. No. 3,255,191.

11. Phenolic compounds having the formula $$[Q-C_zH_{2z}-COO-C_zH_{2z}]_p-R'''-(R)_{4-p}$$

wherein p is an integer from 2 to 4 and
R''' is a tetravalent radical selected from
aliphatic hydrocarbons having from 1 to 30 carbon atoms
aliphatic mono and dithioethers having from 1 to 30 carbon atoms
aliphatic mono and diethers having from 1 to 30 carbon atoms and
z is an integer from 0 to 6.
Illustrative examples of such compounds are

SUB-CLASS I n-Octadecyl 3-(3,5-di-t-butyl-4-hydroxyphenyl)-propionate
n-Octadecyl 2-(3,5-di-t-butyl-4-hydroxyphenyl)-acetate
n-Octadecyl 3,5-di-t-butyl-4-hydroxybenzoate
n-Hexyl 3,5-di-t-butyl-4-hydroxyphenylbenzoate
n-Dodecyl 3,5-di-t-butyl-4-hydroxyphenylbenzoate
Neo-dodecyl 3-(3,5-di-t-butyl-4-hydroxyphenyl)-propionate Dodecyl β-(3,5-di-t-butyl-4-hydroxyphenyl)-propionate
Ethyl α-(4-hydroxy-3,5-di-t-butylphenyl)-isobutyrate
Octadecyl α-(4-hydroxy-3,5-di-t-butylphenyl)-isobutyrate
Octadecyl α-(4-hydroxy-3,5-di-t-butylphenyl)-propionate.

SUB-CLASS II 2-(n-octylthio)ethyl 3,5-di-t-butyl-4-hydroxybenzoate
2-(n-octylthio)ethyl 3,5-di-t-butyl-4-hydroxy-phenylacetate
2-(n-octadecylthio)ethyl 3,5-di-t-butyl-4-hydroxyphenylacetate
2-(n-octadecylthio)ethyl 3,5-di-t-butyl-4-hydroxy benzoate
2-(2-hydroxyethylthio)ethyl 3,5-di-t-butyl-4-hydroxybenzoate
2,2'-Thiodiethanol bis(3,5-di-t-butyl-4-hydroxyphenyl)acetate
Diethyl glycol bis-[3,5-di-t-butyl-4-hydroxyphenyl)-propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5di-t-butyl-4-hydroxybenzoate 2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate.

SUB-CLASS III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentacethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris-[3-3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl)propionate].

The above phenolic ester stabilizers of sub-classes I, II and III are more fully described in U.S. Pat. No. 3,330,859.

12. Phenolic compounds having the formula

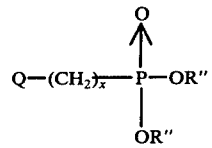

where x is an integer of 1 or 2.

Illustrative examples of such compounds are
Di-n-octadecyl 3,5-di-t-butyl-4-hydroxybenzyl-phosphonate
Di-n-octadecyl 3-t-tubtyl-4-hydroxy-5-methyl-benzylphosphonate
Di-n-octadecyl 1-(3,5-di-t-butyl-4-hydroxyphenyl)-ethanephosphonate
Di-n-tetradecyl 3,5-di-t-butyl-4-hydroxybenzylphosphonate
Di-n-hexadecyl 3,5-di-t-butyl-4-hydroxybenzylphosphonate
Di-n-docosyl-3,5-di-t-butyl-4-hydroxybenzylphosphonate
Di-n-octadecyl 3,5-di-t-butyl-4-hydroxybenzylphosphonate.

The above di-(higher)alkyl phenolic phosphonates are more fully described in U.S. Pat. No. 3,281,505.

(13) Phenolic compounds having the formula

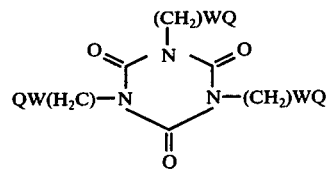

wherein W and Q are defined above.

Illustrative examples of such compounds are:
tris-(3,5-di-t-butyl-4-hydroxybenzyl)isocyanurate
tris-(3-t-butyl-4-hydroxy-5-methylbenzyl)isocyanurate.

The above hydroxyphenylalkenyl isocyanurates are more fully described in U.S. Pat. No. 3,531,483.

The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:
phenyl-1-naphthylamine
phenyl-2-naphthylamine
N,N'-diphenyl-p-phenyldiamine
N,N'-di-sec. butyl-p-phenylenediamine
6-Ethoxy-2,2,4-trimethyl-1,2-dihydroquinoline 6-Dodecyl-2,2,4-trimethyl-1,2-dihydroquinoline
Mono- and di-octyliminodibenzyl and polymerised 2,2,4-trimethyl-1,2-dihydroquinoline.

Ultraviolet absorbers and light protectants include
a. 2-(2'-hydroxyphenyl)benzotriazoles, for instance 5'-methyl; 3',5'-di-t-butyl;
5'-t-butyl; 5-chloro-3',5'-di-t-butyl;

5-chloro-3'-t-butyl-5'-methyl; 3'-sec.butyl-5'tert.butyl; 3'-[α-methylbenzyl]-5'-methyl-; 3'-[α-methylbenzyl)-5'-methyl-5-chloro-; 4'-octoxy-; 3',5'-di-t-amyl; 3'methyl-5'-carbomethoxyethyl; 5-chloro-3',5'-di-t-amyl derivatives.

b. 2,4-bis-(2'-hydroxyphenyl)-6-alkyl-S-triazines, for instance the 6-ethyl or 6-undecyl derivatives.

c. 2-hydroxybenzophenones, for instance the 4-hydroxy, 4-methoxy, 4-octoxy-, 4-decyloxy-, 4-dodecyloxy-, 4,2',4'-trihydroxy or 2'-hydroxy-4,4'-dimethoxy derivatives.

d. 1,3-Bis(2'-hydroxybenzoyl)-benzenes for instance, 1,3-bis-(2'-hydroxy-4'-hexyloxybenzoyl)benzene 1,3-bis-(2'-hydroxy-4'-octoxybenzoyl)benzene 1,3-bis-(2'-hydroxy-4'-dodecyloxybenzoyl)benzene e. Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl -4-hydroxy-benzoic acid-2,4-di-tert.butyl phenyl ester and - octadecyl ester and -2-methyl-4,6-di-tert. butyl phenyl ester.

f. Acrylates, for instance α-Cyano-β,β-diphenylacrylic acid ethyl- or iso-octyl ester, α-carbomethoxycinnamic acid methyl- or butyl ester and N-(β-carbomethoxyvinyl)-2-methyl indoline.

g. Nickel compounds such as nickel complexes of 2,2'-thiobis-(4-tert. octylphenol), for instance the 1:1 and 1:2 complexes, optionally having other ligands such as n-butylamine, tricthanolamine or N-cyclohexyl-diethanolamine; nickel complexes of bis-(4-tert. octylphenyl) sulphone such as the 2:1 complex, optionally having other ligands such as 2-ethylcaproic acid; nickel dibutyl dithiocarbamates; nickel salts of 4-hydroxy-3,5-di-tert.butyl-benzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and h. Oxalie acid diamides, for instance 4,4' -dioctyloxyoxanilide 2,2'-dioctyloxy-5,5'-di-tert.butyl-oxanilide 2,2'-di-dodecyloxy-5,5'-di-tert.butyl oxanilide 2-ethoxy-5-tertiarybutyl-2'-ethyl-oxanilide 2-ethoxy-2'-ethyl-oxanilide mixtures of o- and p-methoxy and ethoxy- di- substituted oxanilides and the compound of formula:

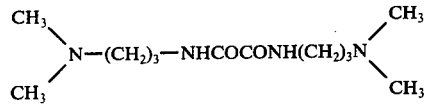

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert. butylphenyl)phosphite.

Peroxide-decamposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid. As with the compound of formula I, any further additive is advantageously employed in a proportion within the range of from 0.01% to 5% by weight, based on the weight of untreated polymeric material.

In binary combinations with one or more antioxidants listed above or in tertiary combinations with such antioxidants and U.V. absorbers listed above, the compounds of formula I provide very effective stabiliser packages in polyolofine formulations.

Some Examples will now be given. Parts and percentages are by weight unless otherwise stated.

The preparation of the 4(4'hydroxyaryl)-3,4-dehydro-2,2,6,6-tetramethylpiperidines used in the examples is described in our co-pending U.S. Pat. application (Case 3-7862/MA.1496/8321/B+).

EXAMPLE 1

4-(4'-Hydroxyphenyl)-2,2,6,6-tetramethylpiperidine 5.0 Parts of 3,4-dehydro-4-(4'-hydroxyphenyl)-2,2,6,6-tetramethylpiperidine were dissolved in 250 parts of ethanol and hydrogenated at room temperature and atmospheric pressure over 0.3 part of platinum oxide catalyst.

When the uptake of hydrogen ceased, the catalyst was separated by filtration and the filtrate evaporated under reduced pressure. The solid was crystallised from a chloroform-petroleum (b.p.60°–80° C) mixture to afford 3.1 parts of the desired product melting at 218°–219° C and having the following elemental analysis:

$C_{15}H_{23}NO$ requires C,77.21;H,9.93;N,6.00, found C,77.01;H,9.70;N,5.73%.

The Examples shown in the following Table I were prepared by a method similar to that used in Example 1.

Table I

| Example Number | $R_1$ | $R_2$ | $R_3$ | $R_4$ | Hydrogenation Solvent and Catalyst | m.p. C° | Molecular Formula | Required (%) C | H | N | Found (%) C | H | N |
|---|---|---|---|---|---|---|---|---|---|---|---|---|---|
| 2 | $CH_3$ | H | H | H | EtOH 5% Pd/C | 170–1 | $C_{16}H_{25}NO$ | 77.68 | 10.19 | 5.66 | 78.01 | 10.22 | 5.53 |
| 3 | $(CH_3)_3C$ | H | H | H | EtOH 5% Pd/C | 223–5 | $C_{19}H_{31}NO$ | 78.84 | 10.79 | 4.84 | 79.10 | 10.73 | 4.64 |
| 4 | $(CH_3)_3C$ | H | H | $CH_3$ | EtOH 5% Pd/C | 172–3 | $C_{20}H_{33}NO$ | 79.15 | 10.96 | 4.69 | 78.93 | 10.85 | 4.51 |

Table I-continued

| Example Number | R₁ | R₂ | R₃ | R₄ | Hydrogenation Solvent and Catalyst | m.p. C° | Molecular Formula | Required (%) C | Required (%) H | Required (%) N | Found (%) C | Found (%) H | Found (%) N |
|---|---|---|---|---|---|---|---|---|---|---|---|---|---|
| 5 | (CH₃)₂CH | H | H | (CH₃)₂CH | EtOH 5% Pd/C | 155-6 | $C_{21}H_{30}NO$ | 79.44 | 11.11 | 4.41 | 79.72 | 11.17 | 4.15 |
| 6 | Cyclohexyl | H | H | H | EtOH 5% Pd/C | 210-2 | $C_{21}H_{33}NO$ | 79.95 | 10.54 | 4.44 | 80.24 | 10.61 | 4.16 |
| 7 | PhCH₂ | H | H | H | MeOH | 183-5 | $C_{22}H_{29}NO$ | 81.69 | 9.04 | 4.33 | 81.83 | 9.21 | 3.92 |

EXAMPLE 8

4-(3′,5′-dimethyl-4′-hydroxyphenyl)-2,2,6,6-tetramethylpiperidine.

15.0 Parts of 3,4-dehydro-4-(3′5′-dimethyl-4′-hydroxyphenyl)-2,2,6,6-tetramethylpiperidine were dissolved in 200 parts of ethanol and allowed to stand over several parts of Raney nickel for 1 hour. The nickel catalyst was separated by filtration and the solution hydrogenated over 2.5 parts of 5% palladium on carbon in an autoclave at 80 atmospheres hydrogen pressure and at 80° C. When the uptake of hydrogen ceased the catalyst was filtered and the filtrate evaporated to dryness. The solid obtained was crystallised from a chloroform-petroleum (b.p. 60°–80°) mixture to afford 11 parts of the desired product melting at 152°–4° and having the following elemental analysis:

$C_{17}H_{27}NO$ required C,78.11; H,10.41; N,5.36, found C77.99; H,10.03; N,5.00%.

EXAMPLE 9

4(4′-hydroxyphenyl)-2,2,6,6-tetramethylpiperidine hydrochloride.

6 Parts of 4(4′-hydroxyphenyl)-2,2,6,6-tetramethylpiperidine were dissolved in methanol and treated with excess concentrated hydrochloric acid. The solution was warmed at 50° for 15 minutes and then evaporated to dryness under reduced pressure. The solid residue was crystallised from a chloroform -methanol-petroleum (b.p. 60°–80° C) mixture to afford 6.0 parts of the desired product melting at > 300° and having the following elemental analysis.

$C_{15}H_{24}NClO$ requires C,66.78; H,8.96; N,5.19; Cl,13.14, Found C,66.92; H,9.00; N,5.08; Cl,13.48%.

EXAMPLE 10

4(4′-hydroxyphenyl)-2,2,6,6-tetramethylpiperidine acetate.

6 Parts of 4(4′-hydroxyphenyl)-2,2,6,6-tetramethylpiperidine were treated with excess acetic acid in a similar manner to Example 9. The residue obtained after evaporation was crystallised from a chloroformmethanol-petroleum mixture to afford 5.7 parts of the desired product melting at 220°–240° and having the following elemental analysis.

$C_{17}H_{27}NO_3$ requires C,69.59; H,9.28; N,4.77, Found C,69.84; H,9.28; N,4.52%.

EXAMPLE 11

4-(3′,5′-Dimethyl-4′-hydroxyphenyl)-2,2,6,6-tetramethylpiperidine-1-oxyl.

14 Parts by weight of 4-(3′,5′-dimethyl-4′-hydroxyphenyl)-2,2,6,6-tetramethylpiperdine and 1 part by weight of benzyl trimethylammonium chloride were dissovled in 170 parts of weight of methanol and treated with a solution of 1 part by weight of sodium tungstate in a little water. Approximately 20 parts by weight of water was added, care being taken to maintain solution. 17 Parts by weight of 30% hydrogen peroxide was dissolved in 30 parts by weight methanol and this solution added dropwise with stirring to the amine solution. When the addition was complete the solution was stirred at room temperature for two hours, and then allowed to stand in the absence of light for two days. The orange crystals were separated and crystallised from ethanol-water to give 7.5 parts by weight of product melting at 163°–5°. A further two parts by weight of product were obtained from the reaction filtrate.

Analysis:

Calculated for $C_{17}H_{26}NO_2$: C,73.87; H,9.48; N,5.07, Found: C,73.66; H,9.59; N,4.87%.

EXAMPLE 12

4-(4′-Hydroxyphenyl)-2,2,6,6-tetramethylpiperidine-1-oxyl.

4.66 Parts by weight of 4-(4′-hydroxyphenyl)-2,2,6,6-tetramethylpiperidine was oxidised by a method similar to that used in the above experiment. After 14 days the methanolic solution was diluted with an equal volume of water and extracted into ether. The aqueous phase was discarded and the ethereal layer washed with 2% sulphuric acid and water. After drying (MgSO₄) the organic phase was evaporated under reduced pressure. The residue obtained was crystallised from methanol-water to give 2.3 parts by weight of product melting at 182°–5°.

Analysis:

Calculated for $C_{15}H_{22}NO_2$: C,72.54; H,8.93; N,5.64. Found: C,72.84; H,8.96; N,5,53%.

EXAMPLE 13

4-(3′,5′-Dimethyl-4′-hydroxyphenyl)-1,2,2,6,6-pentamethylpiperidine.

3.0 Parts by weight of 4-(3′,5′-dimethyl-4′-hydroxyphenyl)-2,2,6,6-tetramethylpiperidine was dissolved in formic acid and treated with 1.0 part by weight of formaldehyde on a stream bath. After heating for 12 hours the solution was cooled and basified in aqueous solution. The basification liquor was extracted into ether, the ethereal layer dried with magnesium sulphate and evaporated under reduced pressure. Crystallisation of the residue from petroleum (b.p. 80°–100°) have 1.9 parts by weight of product melting at 144°–6°.

Analysis:

Calculated for $C_{18}H_{29}NO$: C,78.49; H,10.61; N,5.09. Found: C,78.55; H,10.73; N,5.03%.

EXAMPLE 14

4-(4′-Benzoyloxyphenyl)-2,2,6,6-tetramethylpiperidine 6 Parts of 4 (4′-hydroxyphenyl)-2,2,6,6-tetramethylpiperidine were dissolved in 100 parts of 10% aqueous sodium hydroxide by warming 6 Parts of benzoyl chloride were added and the mixture shaken whilst the alkalinity of the solution was maintained. The precipitate was separated and dissolved in hot water. This solution was basified by the addition of aqueous sodium carbonate solution. The precipitate was separated dissolved in ether and the ethereal solution washed with 10% sodium hydroxide solution and water. The organic phase was dried over magnesium sulphate and evaporated under reduced pressure. The residue was crystallised from petroleum (b.p. 60°-80°) to yield 3 parts of the desired product melting at 127°-8° and having the following elemental analysis.

$C_{22}H_{27}NO_2$: requires C,78.30; H,8.06; N,4.15.
found: C,78.60; H,8.23; N,4.43%.

EXAMPLE 15

4-(3',5'-Dimethyl-4'-octanoyloxyphenyl) 2,2,6,6-tetramethylpiperidine

20 Parts of 4-(3',5'-dimethyl-4'-hydroxyphenyl)-2,2,6,6-tetramethylpiperidine were dissolved in 1000 parts of sodium dried xylene and heated to reflux whilst stirred. 6.3 Parts of octanoyl chloride dissolved in a small amount of xylene were added to the refluxing solution dropwise. The solution was heated at reflux overnight, allowed to cool and filtered. The filtrate was evaporated to low bulk, dissolved in ether and washed with 2% aqueous sodium hydroxide and water. The organic phase was dried over magnesium sulphate and evaporated under reduced pressure. The residue was distilled under reduced pressure to yield 10.3 parts of the desired product having boiling point 175°-178°/0.05 mm and the following elemental analysis $C_{25}H_{41}NO_2$: requires C,77.47; H,10.66; N,3.61.
found: C,77.50; H,10.50; N,3.59%.

EXAMPLE 16

4(4'-N-Methylcarbamoyloxyphenyl)-2,2,6,6-tetramethylpiperidine

2 Parts of 4(4'-N-Methylcarbamoyloxyphenyl) 3,4-dehydro-2,2,6,6-tetramethylpiperidine were dissolved in 100 parts of methanol and hydrogenated at atmospheric pressure and temperature over 0.7 parts of 5% palladium on carbon. The catalyst was separated and the solvent evaporated under reduced pressure. The residue was crystallised from petroleum b.p.(80°-100°) to yield 1.5 parts of the desired product melting at 133°-4° and having the following elemental analysis.

$C_{17}H_{26}N_2O_2$: requires C,70.31; H,9.02; N,9.65.
found: C,70.40; H,9.02; N,9.44%.

EXAMPLES 17 to 23

38 Parts of polypropylene were homogenised with 0.76 part of n-octadecyl-β-(4'-hydroxy-3',5'-t-butylphenyl) propionate in a kneading machine over a period of 3 minutes at 200° C. 0.19 part of the product of one of Examples 1, 8 and 13, 7, 12, 11, 14 were then added and homogenisation continued for another 7 minutes.

This composition was compression moulded into films of 0.1 mm. thickness at 260° C for 6 minutes and the films so obtained were then quenched in cold water.

A section measuring 44 × 100 mm. was separated from the 0.1 mm. annealed polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3000 Angstrom units; the blacklight lamps were 2 feet long, 20-watt ultraviolet lamps characterised by a peak emission of 3500 Angstrom units. The sample was rotated concentrically within the bank of lamps so that the radiation therefrom was uniformly distributed over the section under test.

The exposed sample was examined periodically and the time (T) at which the sample reached 50% of the initial elongation at break was noted.

The time (Tc) for the elongation of a control sample (not containing the product of Example 1) to decrease to 50% of the initial elongation was then determined.

The performance of the compound of formula I as a light stabiliser could then be assessed by determining the factor T/Tc. The results obtained are summarised in the following Table II:

TABLE II

| Example | Additive | Time to 50% initial elongantion at break (hours) |
|---|---|---|
| — | None | 125 |
| 17 | 4-(4'-hydroxyphenyl)-2,2,6,6-tetramethylpiperidine | 380 |
| 18 | 4-(3',5'-dimethyl-4'-hydroxyphenyl)-2,2,6,6-tetramethylpiperidine | 670 |
| 19 | 4-(3',5'-dimethyl-4'-hydroxyphenyl)-1,2,2,6,6-pentamethylpiperidine | 695 |
| 20 | 4-(3'-benzyl-4'-hydroxyphenyl)-2,2,6,6-tetramethylpiperidine | 380 |
| 21 | 4-(4',hydroxyphenyl)-2,2,6,6-tetramethylpiperidine-1-oxyl | 540 |
| 22 | 4-(3',5'-dimethyl-4'hydroxyphenyl)-2,2,6-tetramethylpiperidine-1-oxyl | 320 |
| 23 | 4-(4'-Benzoyloxyphenyl)-2,2,6,6-tetramethylpiperidine | 510 |

The results in the Table demonstrate clearly the improved light stability of the polypropylene foil containing a stabiliser according to this invention compared with a control polypropylene foil.

EXAMPLE 24

1000 Parts by weight of unstabilised polypropylene powder were thoroughly dry-blended with 1 part by weight of n-octadecyl-β-(4'-hydroxy-3',5'-di-t-butylphenyl) propionate and 2 parts by weight of 4-(4'-benzoyloxyphenyl)-2,2,6,6-tetramethylpiperidine.

The dry blend was extruded at cylinder temperatures of from 180° to 220° C, and the resulting strand was granulated. The stabilised formulation so obtained was melt-spun and stretched under the following conditions:

| | |
|---|---|
| Extruder temperatures | 230/265/275° C. |
| Melt temperature at the dye | 270° C |
| Spinning speed | 400 m./minute |
| Stretching Ratio | 1 : 5 |
| Titer of Multifilament | 130/137 denier |
| Tensile Strength | 6 g./denier |

The multifilament obtained was mounted on a sample holder of a Xenotest 150 apparatus (Quarzlampen GmbH) using white cardboard as backing. In intervals of 200 hours of exposure time, 5 fibre samples are measured for their retained tensile strength. The data obtained are plotted against exposure time and the exposure time (T) to give 50% loss of original tensile strength is derived from the graph. This value is taken as the failure time.

TABLE III

| Example | Light stabiliser | Time (T) to 50% retained tensile strength (hours) | Facta T (stabilized) T (control) |
|---|---|---|---|
| — | none | 800 | 1.0 |
| — | 2-(2'-hydroxy-3'5'-di-t-butylphenyl)-5-chlorobenzotriazole | 1630 | 2.0 |
| 24 | 4-(4'-benzoyloxy-phenyl)-2,2,6,6-tetra-methylpiperidine | 3350 | 4.2 |

EXAMPLE 25

4(4'-n-Butyloxyphenyl)-2,2,6,6-tetramethylpiperidine

1 Part of 4-(4-hydroxyphenyl)-2,2,6,6-tetramethylpiperidine was dissolved in warm ethanol and treated with 0.172 parts of sodium hydroxide dissolved in ethanol. The solution was stirred and heated to reflux whilst 0.65 parts of n-butyl bromide dissolved in ethanol was added. The solution was heated at reflux overnight and then evaporated under reduced pressure. The residue was dissolved in ether and washed with water, sodium hydroxide solution (3%) and further water. The organic layer was dried (MgSO$_4$) and evaporated under reduced pressure. The residue was distilled to yield the desired product having b.p. 160°/0.2 mm. and the following elemental analysis:

$C_{19}H_{31}NO$: requires C,78.84; H,10.79; N,4.84.
found: C,78.96; H,10.78; N,4.55%.

EXAMPLE 26

4-(4-n-Dodecyloxyphenyl)-2,2,6,6-tetramethylpiperidine Prepared by a method similar to that employed in Example 25. The residue obtained after alkali extraction was distilled to yield the desired product having b.p. 195°/0.1 mm and the following elemental analysis:

$C_{27}H_{47}NO$: requires C,80.74; H,11.79; N,3.49.
found: C,80.50; H,11.59; N,3.27.

EXAMPLE 27

4-(4-Benzyloxyphenyl)-2,2,6,6-tetramethylpiperidine Prepared by a method similar to that employed in Example 25. The residue obtained after alkali extraction was recrystallised from a methanol-water mixture to yield the desired product melting at 107-9° and having the following elemental analysis:

$C_{22}H_{29}NO$: ½ $H_2O$ requires C,79.50; H,9.10; N,4.20.
found: C,79.47; H,9.11; N,3.93%.

What is claimed is:

1. A compound of the formula I

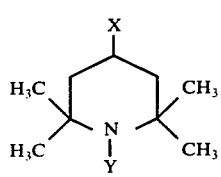

or a salt thereof, wherein the substituent X has one of the formulae

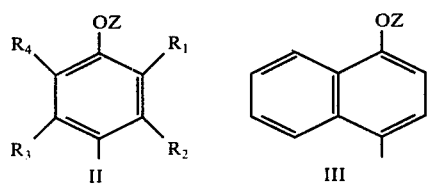

wherein $R_1$, $R_2$, $R_3$ and $R_4$ are the same or different and each is hydrogen, a straight- or branched-chain alkyl residue having from 1 to 9 carbon atoms, a cycloalkyl residue having from 5 to 14 carbon atoms, an aralkyl residue having from 7 to 14 carbon atoms or an aryl or alkaryl residue having from 6 to 14 carbon atoms, Y is hydrogen, O, a straight- or branched-chain alkyl residue having from 1 to 12 carbon atoms, an alkenyl or alkynyl residue having from 3 to 12 carbon atoms or an aralkyl residue having from 7 to 12 carbon atoms.

Z is hydrogen, an alkyl residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 12 carbon atoms, an aromatic residue having from 6 to 12 carbon atoms or a β-hydroxyethyl, β-cyonoethyl, furan or thiophene residue or the group —$COZ_1$ wherein $Z_1$ has the same significance as Z, or $Z_1$ is a group having the formula —$NR_5R_6$ wherein $R_5$ is hydrogen or an alkyl residue having from 1 to 4 carbon atoms, and $R_6$ is hydrogen, an aliphatic residue having from 1 to 20 carbon atoms, a cycloaliphatic residue having from 5 to 12 carbon atoms or an aromatic residue having from 6 to 12 carbon atoms.

2. A compound according to claim 1 wherein X has the formula II and Z is hydrogen, an alkyl residue having from 1 to 12 carbon atoms, an allyl or methallyl residue a cyclopentyl or cyclohexyl residue, a benzyl α,α-dimethylbenzyl or α-methyl benzyl residue, a phenyl, tolyl, naphthyl or p-t-butyl phenyl residue, or a furan B-hydroxyethyl, B-cyanoethyl, or thiophene residue.

3. A compound according to claim 1 having the formula

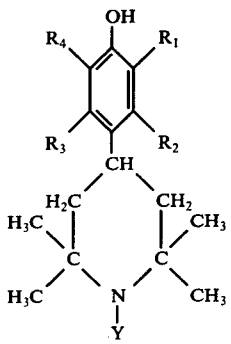

wherein $R_1$ and $R_4$ are selected from hydrogen, methyl, ethyl, n-propyl, isopropyl, sec-butyl, t-butyl, 1,1-dimethylpropyl, 1,1-dimethylbutyl, 2-octyl, cyclohexyl, 1-methylcyclohexyl, benzyl, α,α-dimethylbenzyl and phenyl residues, $R_2$ and $R_3$ are hydrogen, methyl or ethyl groups and Y is hydrogen, O or methyl.

4. A compound according to claim 1 which is 4-(4'-hydroxyphenyl-2,2,6,6-tetramethylpiperidine.

5. A compound according to claim 1 which is 4-(3'-methyl-4'-hydroxyphenyl)-2,2,6,6-tetramethylpiperidine.

6. A compound according to claim 1 which is 4-(3'-t-butyl-4'-hydroxyphenyl)-2,2,2,6-tetramethyl-piperidine.

7. A compound according to claim 1 which is 4-(3',5'-di-isopropyl-4'-hydroxyphenyl)-2,2,6,6-tetramethylpiperidine.

8. A compound according to claim 1 which is 4-(3',5'-dimethyl-4'-hydroxyphenyl)-2,2,6,6-tetramethylpiperidine.

* * * * *